United States Patent [19]

Nakahara et al.

[11] Patent Number: 4,540,728
[45] Date of Patent: Sep. 10, 1985

[54] DIALLYL-1,3,5-TRIAZINO-4-(2,2,6,6-TETRAMETHYL PIPERIDYL) AMINES AS MONOMERS AND POLYMERS AND STABILIZED SYNTHETIC RESIN COMPOSITIONS

[75] Inventors: Yutaka Nakahara, Iwatsuki; Ryoji Kimura, Urawa, both of Japan

[73] Assignee: Adeka Argus Chemical Co., Ltd., Urawa, Japan

[21] Appl. No.: 531,147

[22] Filed: Sep. 9, 1983

[30] Foreign Application Priority Data

Sep. 13, 1982 [JP] Japan .................. 57-159198

[51] Int. Cl.³ .............................................. C08K 5/34
[52] U.S. Cl. .................... 524/100; 526/261; 528/423; 544/209; 544/212; 544/207
[58] Field of Search ............... 524/100; 526/261; 528/423; 544/198, 209, 212, 207

[56] References Cited

U.S. PATENT DOCUMENTS

| 4,241,208 | 12/1980 | Murayama et al. | 546/19 |
| 4,356,287 | 10/1982 | Loffelman et al. | 525/204 |
| 4,387,225 | 6/1983 | Douglas et al. | 544/212 |

FOREIGN PATENT DOCUMENTS

| 15490 | 8/1963 | Japan | 526/261 |

*Primary Examiner*—John Kight
*Assistant Examiner*—Kriellion Morgan

[57] ABSTRACT

Polymers of diallyl-1,3,5-triazino-4-(2,2,6,6-tetramethyl piperidyl) amines are provided, having a molecular weight within the range from about 800 to about 20,000, and derived from the monomer:

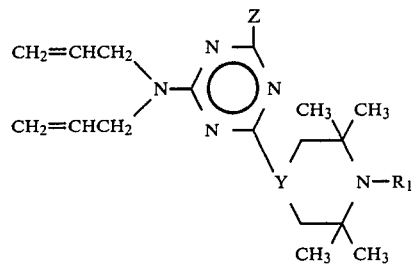

wherein:
$R_1$ is selected from the group consisting of hydrogen; oxyl; alkyl and hydroxyalkyl having from one to about eighteen carbon atoms; alkylaryl having from seven to about eighteen carbon atoms; epoxy alkyl having from three to about eighteen carbon atoms; and acyl having from two to about eighteen carbon atoms;

Y is selected from the group consisting of

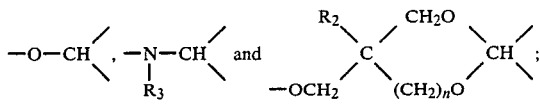

where $R_2$ and $R_3$ are hydrogen or alkyl having from one to about eight carbon atoms and n is 0 or 1;

Z is selected from the group consisting of

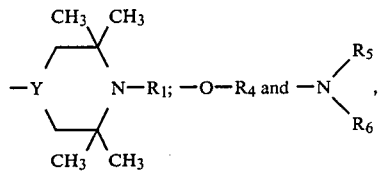

in which $R_4$, $R_5$ and $R_6$ are selected from the group consisting of hydrogen; alkyl having from one to about eighteen carbon atoms; cycloalkyl having from three to about twelve carbon atoms; and aryl having from six to about thirty carbon atoms; as well as stabilized synthetic resin compositions having an improved resistance to deterioration by light and containing such a polymer.

33 Claims, No Drawings

DIALLYL-1,3,5-TRIAZINO-4-(2,2,6,6-TETRAMETHYL PIPERIDYL) AMINES AS MONOMERS AND POLYMERS AND STABILIZED SYNTHETIC RESIN COMPOSITIONS

It is known that polymers such as polyethylene, polypropylene, ABS resin, polyvinyl chloride and polyurethanes are subject to degradation when exposed to ultraviolet light, as evidenced by discoloration and a deterioration in mechanical strength.

Therefore, various kinds of light stabilizers have been proposed to prevent such deterioration. However, many conventional stabilizers are unsatisfactory, in their stabilizing effect or are unstable to heat and oxidation, or are extracted by water or organic solvents. Some conventional stabilizers impart color to the polymers.

Piperidine compounds do not impart color to the polymer, and act as quenchers, but many are unsatisfactory in their stabilizing effect, are volatilized out from the polymer at high temperature, and are extracted by water.

To avoid these difficulties, various high molecular weight hindered piperidine compounds have been proposed.

Cantatore U.S. Pat. No. 4,104,248 patented Aug. 1, 1978, discloses polyamines of the general formula:

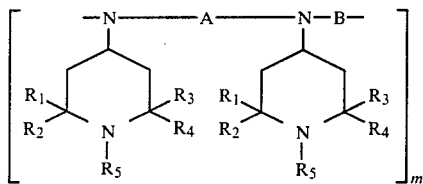

wherein $R_1$, $R_2$, $R_3$ and $R_4$ are equal to or different from each other and are an alkyl group having from 1 to 4 carbon atoms;

$R_5$ is either hydrogen or an alkyl group having from 1 to 4 carbon atoms;

A is an alkylene group having from 2 to 10 carbon atoms;

B is a divalent aliphatic, cycloaliphatic, aromatic or alkylaromatic radical, containing optionally hetero atoms such as O, S, N and P in the chain or as side substituents; and n is a whole number between 2 and 1000, these are said to exert a stabilizing action on polymers both as such as well as in the form of fibers, films, or other shaped articles.

Rody and Rasberger U.S. Pat. No. 4,233,412, patented Nov. 11, 1980, discloses condensation polymers and addition polymers, the recurrent molecular unit of which contains a polyalkylpiperidine radical of the formula

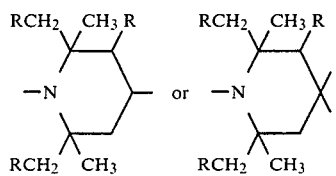

or is substituted by a polyalkylpiperidine side group of the formula

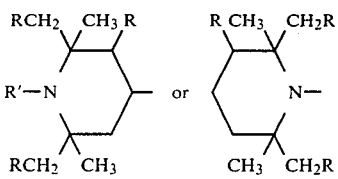

in which R denotes hydrogen or alkyl with 1–5 C atoms and R′ denotes hydrogen, alkyl with 1–12 C atoms, alkenyl with 3–8 C atoms, alkinyl with 3–6 C atoms, aralkyl with 7–12 C atoms, alkanoyl with 1–8 C atoms or alkenoyl with 3–5 C atoms, and to copolymers with one another or with polyalkylpiperidine-free components.

Such condensation polymers and addition polymers include those polymers or oligomers which are manufactured by a polycondensation reaction or polyaddition reaction and possess hetero-atoms in the polymer chain. Examples of such polymers are polyesters, polyethers, polyamides, polyamines, polyurethanes, polyureas, polysulphides, polysulphones, polyimides, polysulphonates, polyphosphates, polyphosphonates, polysilyl esters, polysiloxanes, polyhydrazides, polyhydrazenes or polybenzimidazoles.

Karrer U.S. Pat. No. 4,294,949, patented Oct. 13, 1981, discloses homopolymeric compounds which carry N-heterocyclic rings in a side position and have the recurring structural unit of the formula I

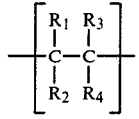

in which $R_1$ is a group containing an N-heterocyclic ring, of the formulae II, III, IV and V.

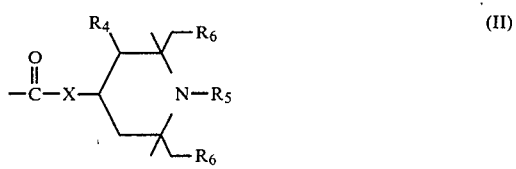

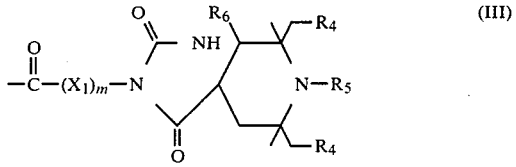

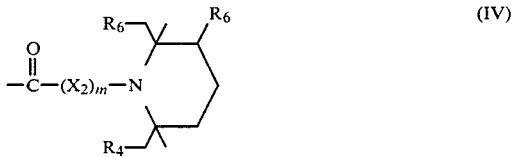

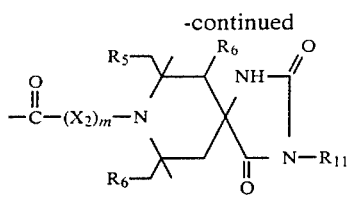

(V)

in which $R_5$ is hydrogen, oxyl, $C_1$-$C_{18}$ alkyl, 2-hydroxyethyl, 2-hydroxypropyl, $C_3$-$C_8$ alkenyl, $C_3$-$C_6$ alkynyl, $C_7$-$C_{12}$ aralkyl, $C_2$-$C_{21}$ alkoxyalkyl, an aliphatic acyl group having 1-4 C atoms or one of the groups —$CH_2COOR_7$ or —$COOR_8$, in which $R_7$ is $C_1$-$C_{12}$ alkyl, $C_3$-$C_8$ alkenyl, phenyl, $C_7$-$C_8$ aralkyl or cyclohexyl and $R_8$ is $C_1$-$C_{12}$ alkyl, phenyl, benzyl or cyclohexyl, and $R_6$ is hydrogen or $C_1$-$C_4$ alkyl and Y is

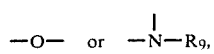

in which $R_9$ is hydrogen, $C_1$-$C_{12}$ alkyl, $C_7$-$C_{12}$ aralkyl or cyclohexyl, and $X_1$ is a group of the formula —O—$CH(R_{10})$—$CH_2$—(VI) or denotes —O—$CH_2$—$CH_2$—$CH_2$—, in which $R_{10}$ is hydrogen, methyl, ethyl, phenoxymethyl or phenyl, and n is 0 or 1, and $X_2$ is a group of the formula VI, in which $R_{10}$ is as defined above, or a group of the formula —O—$CH_2$—CH(OH)—$CH_2$—(VII), and m is 0 or 1, and $R_{11}$ is $C_1$-$C_{18}$ alkyl or is cyclohexyl, phenyl or benzyl which are unsubstituted or substituted by $C_1$-$C_4$ alkyl or $C_1$-$C_4$ alkoxy, and $R_2$ is hydrogen or $C_1$-$C_4$ alkyl, and, if $R_2$ and $R_4$ are hydrogen, $R_1$ and $R_3$ together form a group of the formula VIII

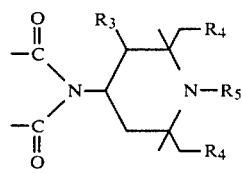

(VIII)

in which $R_5$ and $R_6$ are as defined above and $R_3$ is hydrogen or $C_1$-$C_2$ alkyl and $R_4$ is hydrogen or methyl, or their copolymers which compounds containing at least one polymerisable double bond, the molar ratio of the component of the formula I to the comonomer component being up to 1:10.

$R_1$ can be a group of the formulae II, III, IV or V. Preferably, $R_1$ is a group of the formulae II or IV.

Wiezer, Pfahler and Mayer U.S. Pat. No. 4,308,362, patented Dec. 29, 1981, discloses copolymers of one or several polyalkyl piperidines of the formula (I)

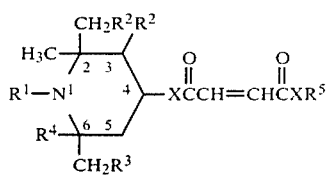

(I)

and one or several comonomers of the formula (II)

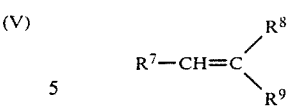

(II)

with a molecular weight of from about 1000 to about 10,000, wherein in the monomers of the formula (I)

$R_1$ is hydrogen or $C_1$ to $C_{18}$ alkyl, preferably hydrogen or $C_1$ to $C_4$ alkyl and especially hydrogen, $R_2$ and $R_3$ are either the same and represent hydrogen or $C_1$ to $C_5$ alkyl, preferably hydrogen or methyl and especially hydrogen, in which case $R_4$ is methyl, or $R_2$ is hydrogen or $C_1$ to $C_5$ alkyl, in which case $R_3$ and $R_4$, together with the carbon atoms to which they are bound, represent a $C_5$ or $C_6$ cycloalkyl group or a group of the formula (III)

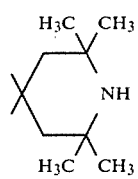

(III)

$R_5$ is hydrogen, $C_1$ to $C_{18}$ alkyl or a group of the formula (IV)

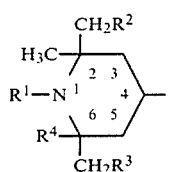

(IV)

in which $R_1$, $R_2$, $R_3$ and $R_4$ are defined as above, but preferably represent hydrogen or $C_1$ to $C_{12}$ alkyl or a group of the formula (IV) and especially hydrogen, $C_1$ to $C_6$ alkyl or a group of the formula (IV), X stands in particular for oxygen and also for a radical —$NR_6$, $R_6$ being hydrogen, $C_1$ to $C_{18}$ alkyl or a group of the formula (IV), preferably hydrogen or $C_1$ to $C_{18}$ alkyl, whereas in the monomers of the formula (II)

$R_7$ is hydrogen or a group of the formula $COOR_{10}$ with $R_{10}$ being $C_1$ to $C_{18}$ alkyl, but preferably hydrogen, $R_8$ is hydrogen or methyl, preferably hydrogen, and $R_9$ is hydrogen or $C_1$ to $C_{36}$ alkyl, preferably hydrogen or $C_1$ to $C_{18}$ alkyl and especially hydrogen, or is phenyl or chlorine, or acetyl, or a group of the formula —$OR_{11}$ with $R_{11}$ being hydrogen or $C_1$ to $C_{18}$ alkyl, or a group of the formula —$COOR_{12}$ with $R_{12}$ being alkyl or hydroxyalkyl with 1 to 18 carbon atoms or a radical of the formula (IV), preferably an alkyl or hydroxyalkyl group of 1 to 6 carbon atoms or a radical of the formula (VI).

Nikles U.S. Pat. No. 4,311,820, patented Jan. 19, 1982, discloses homopolymers and copolymers of vinyl ethers of the formula I

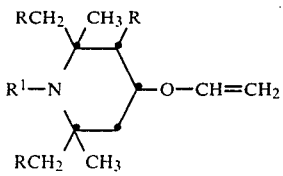

in which R is hydrogen or $CH_3$ and $R_1$ is hydrogen, $C_1$–$C_8$ alkyl, benzyl, allyl, formyl or acetyl. Preferably, R is hydrogen.

Preferred homopolymers and copolymers of vinyl ethers of the formula I are those in which $R_1$ is methyl and in which R is hydrogen.

The homopolymers of vinyl ethers of the formula I are also preferred, especially the homopolymers of 1,2,2,6,6-pentamethyl-4-piperidyl vinyl ether.

The homopolymers, according to the invention, of the vinyl ethers of the formula I in general have an average molecular weight of about 600 to 100,000, which corresponds approximately to a degree of polymerisation of 3 to 500. For use as stabilizers in plastics, polymers with an average molecular weight of about 3,000 to 50,000 are in particular of interest, since in this range not only a good stability to migration and stability to extraction but also an adequate compatibility in the substrate are ensured.

The properties of these polymeric stabilizers can be modified by copolymerisation with a comonomer capable of copolymerisation. Suitable comonomers are, in particular, ethylenically unsaturated compounds, such as alkyl vinyl ethers, for example methyl vinyl ether or isobutyl vinyl ether; vinyl esters, for example vinyl acetate or vinyl propionate; other vinyl compounds, for example styrene, N-vinylpyrrolidone, vinyl chloride or vinylidene chloride; and derivatives of acrylic or methacrylic acid, for example methyl acrylate, tert-butyl acrylate, methyl methacrylate, acrylamide, N-butyl methacrylamide, acrylonitrile or methacrylonitrile, and also maleic acid derivatives, such as esters, amides and cyclic imides of maleic acid.

U.S. Pat. No. 4,356,287 patented Oct. 26, 1982 to Loffelman and Brady, discloses polymers prepared by the polymerisation of a monomer represented by formula (I)

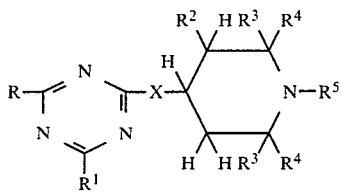

wherein R represents $C_3$–$C_6$ alkenyloxy, $C_3$–$C_6$ alkenylamino, or di($C_3$–$C_6$ alkenyl) amino; $R^1$ represents $C_1$–$C_8$ alkyl, $C_1$–$C_8$ alkoxy, halo, $C_1$–$C_8$ alkylthio, $C_3$–$C_6$ alkenyloxy, amino, $C_3$–$C_6$ alkenylamino, di($C_3$–$C_6$ alkenyl) amino, the groups

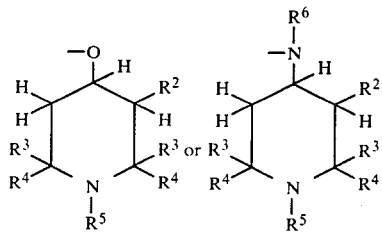

wherein $R^2$, $R^3$, $R^4$, $R^5$, and $R^6$ are as defined below, $C_1$–$C_{18}$ alkylamino, $C_1$–$C_{18}$ dialkylamino, morpholino, piperidino, pyrrolidyl, a substituted $C_1$–$C_{18}$ alkylamino, or a substituted $C_1$–$C_{18}$ dialkylamino, wherein the substituents are selected from amino, cyano, carboxy, alkoxycarbonyl wherein the alkoxy moiety has 1 to 8 carbon atoms, and the groups

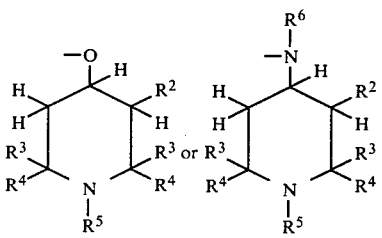

wherein $R^2$ represents hydrogen, $C_1C_8$ alkyl, or benzyl; $R^3$ and $R^4$ independently represent $C_1$–$C_8$ alkyl, benzyl, or phenethyl, or together with the carbon to which they are attached form a $C_5$–$C_{10}$ cycloalkyl; and $R^5$ represents hydrogen, $C_2$–$C_3$ hydroxyalkyl, $C_1$–$C_8$ alkyl, hydroxyl, or oxyl; $R^6$ represents hydrogen, $C_1$–$C_8$ alkyl, or

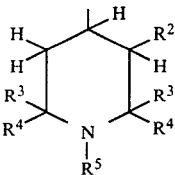

wherein $R^2$, $R^3$, $R^4$, and $R^5$ are as previously defined; and X is oxy, or

wherein $R^6$ is as previously defined.

U.S. Pat. No. 4,369,274, patented Jan. 18, 1983, to Thomas, discloses diallylamine derivatives of the formula:

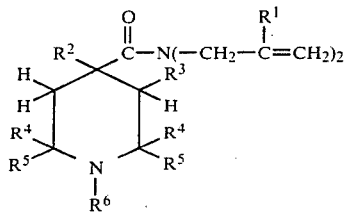

wherein $R^1$ represents hydrogen, or $C_1$–$C_4$ alkyl, $R^2$ represents hydrogen, hydroxy, or $C_1$–$C_8$ alkoxy; $R^3$ represents hydrogen, $C_1$–$C_8$ alkyl, or benzyl; $R^4$ and $R^5$ independently represent $C_1$–$C_8$ alkyl, benzyl, or phenethyl, or together with the carbon to which they are attached form a $C_5$–$C_{10}$ cycloalkyl; and $R^6$ represents hydrogen, $C_2$–$C_3$ hydroxyalkyl, $C_1$–$C_8$ alkyl, hydroxy, or oxyl, and homopolymers thereof.

In accordance with the present invention, polymers of diallyl-1,3,5-triazino-4-(2,2,6,6-tetramethyl piperidyl-)amines are provided, having a molecular weight within the range from about 800 to about 20,000, and derived from the monomer:

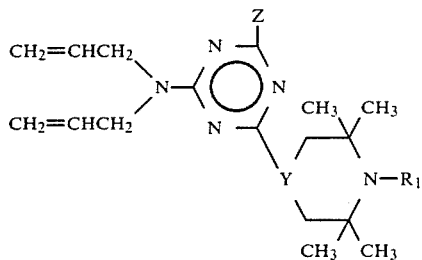

wherein:
$R_1$ is selected from the group consisting of hydrogen; oxyl; alkyl and hydroxyalkyl having from one to about eighteen carbon atoms; alkylaryl having from seven to about eighteen carbon atoms; epoxy alkyl having from three to about eighteen carbon atoms; and acyl having from two to about eighteen carbon atoms;

Y is selected from the group consisting of

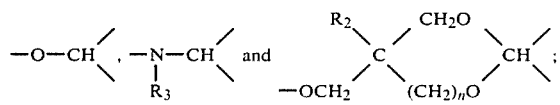

where $R_2$ and $R_3$ are hydrogen or alkyl having from one to about eight carbon atoms and n is 0 or 1;

Z is selected from the group consisting of

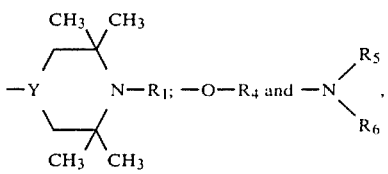

in which $R_4$, $R_5$ and $R_6$ are selected from the group consisting of hydrogen; alkyl having from one to about eighteen carbon atoms; cycloalkyl having from three to about twelve carbon atoms; and aryl having from six to about thirty carbon atoms.

There are also provided stabilized synthetic resin compositions having an improved resistance to deterioration by light and containing such a polymer.

There are three subgeneric types of these monomers, varying according to the Y group:

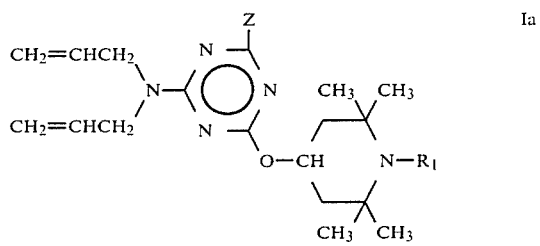

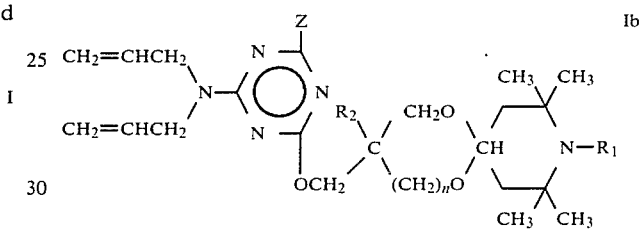

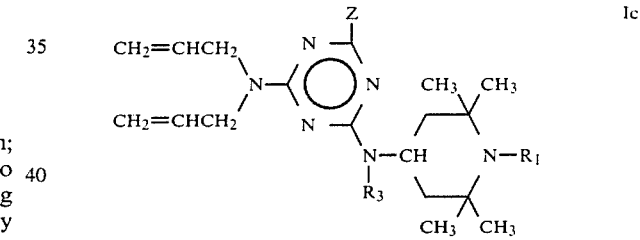

Exemplary $R_1$, $R_4$, $R_5$ and $R_6$ alkyl are methyl, ethyl, propyl, isopropyl, butyl, amyl, hexyl, heptyl, octyl, 2-ethylhexyl, nonyl, decyl, dodecyl, octadecyl, benzyl, phenylethyl, 2-hydroxyethyl, 2-hydroxypropyl, 2-hydroxybutyl and 2,3-epoxypropyl;

Exemplary $R_1$ acyl are acetyl, propionyl, butyroyl, acryloyl, methacryloyl, octanoyl and benzoyl;

Exemplary $R_2$ and $R_3$ alkyl include methyl, ethyl, propyl, butyl; isobutyl; tert-butyl, amyl, isoamyl, hexyl, 2-ethylhexyl, isooctyl and octyl;

Exemplary $R_4$, $R_5$ and $R_6$ cycloalkyl include cyclopropyl, cyclobutyl, cyclopentyl, cyclohexyl, cycyloctyl, and cyclododecyl;

Exemplary $R_4$, $R_5$ and $R_6$ aryl include phenyl, naphthyl, tolyl, xylyl, t-butylphenyl, nonylphenyl, octylphenyl, 2,4-di-t-butylphenyl and dinonylphenyl.

Examples of monomer compounds represented by Formula I are shown below.

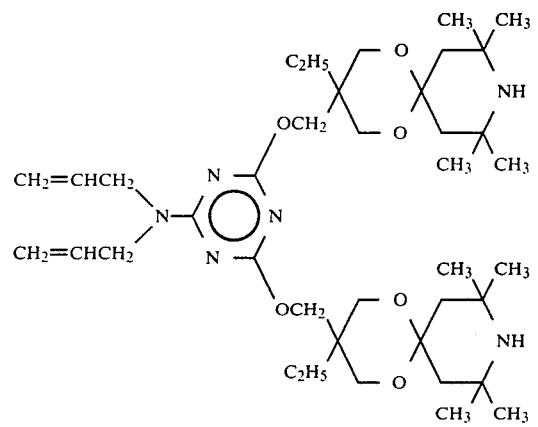
1.
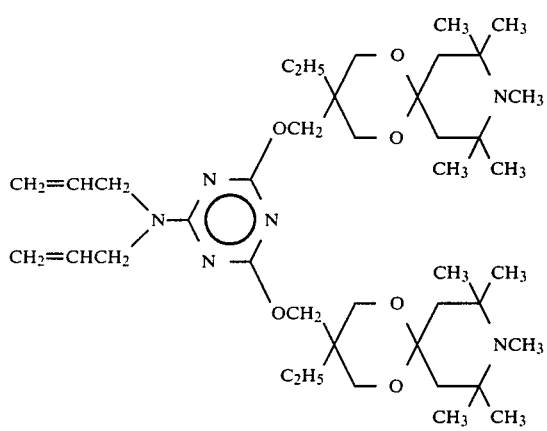
2.
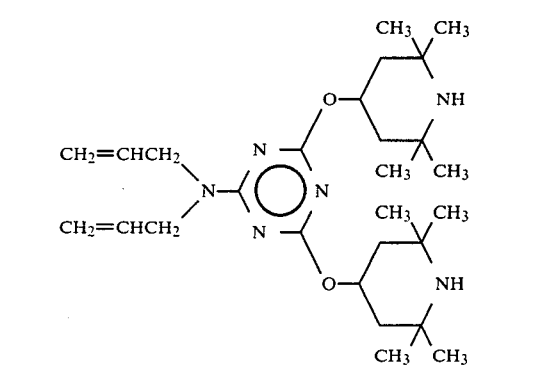
3.
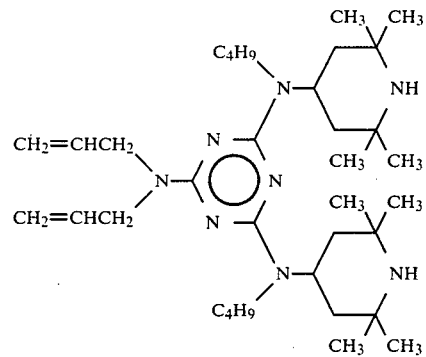
4.
-continued
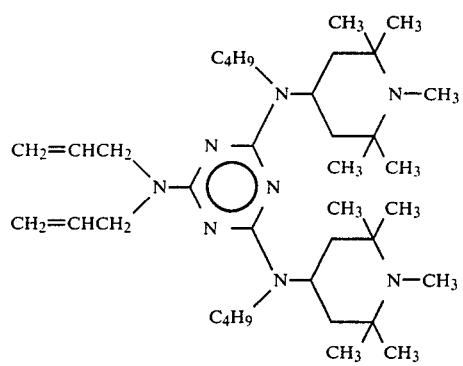
5.
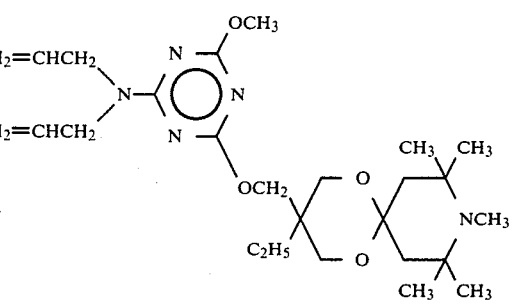
6.
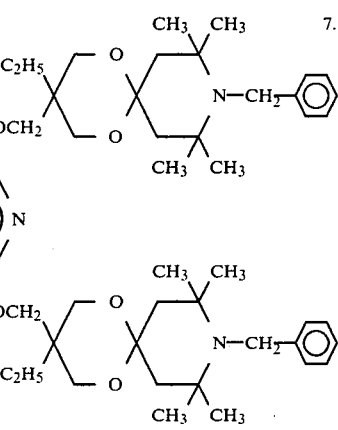
7.
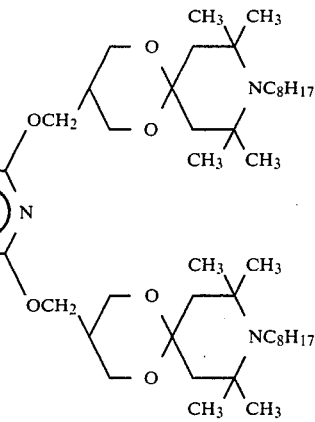
8.

-continued
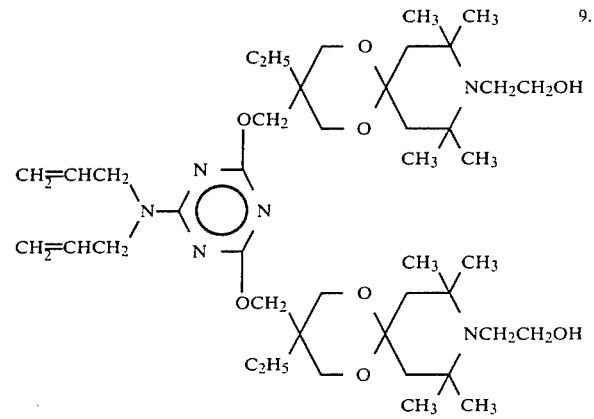
9.
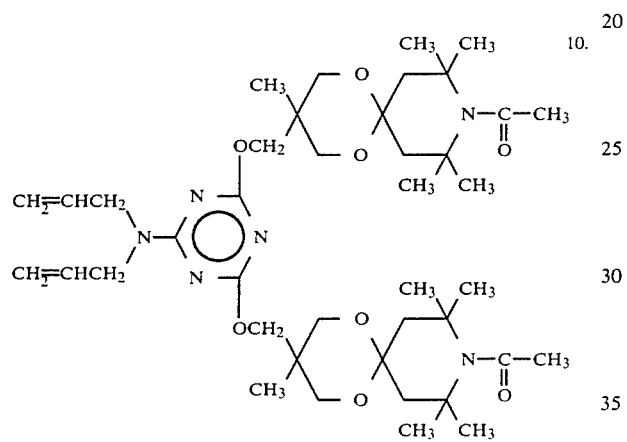
10.
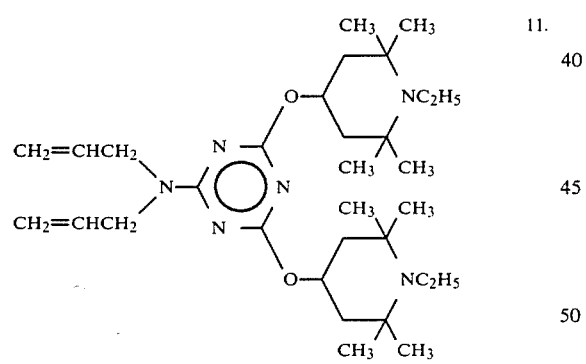
11.
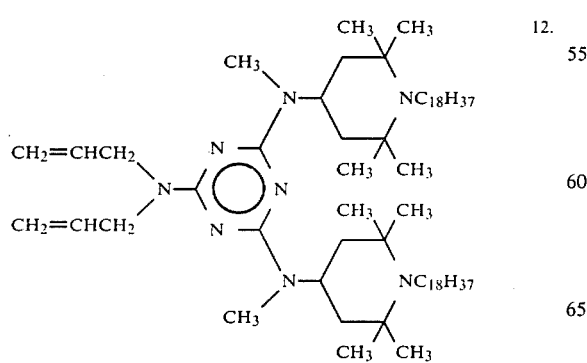
12.
-continued
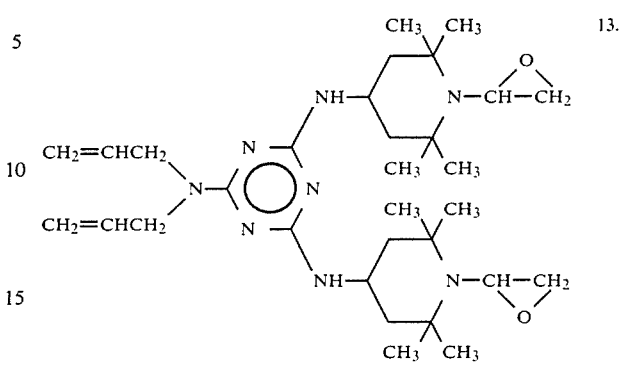
13.
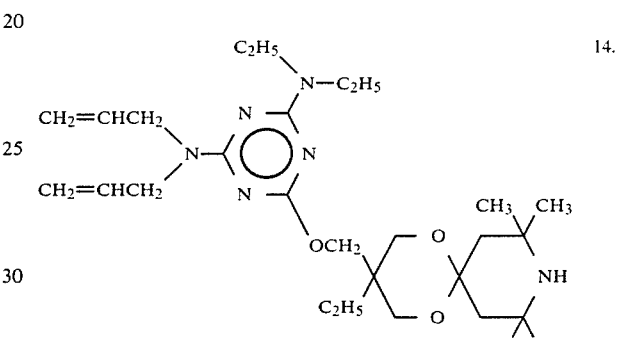
14.
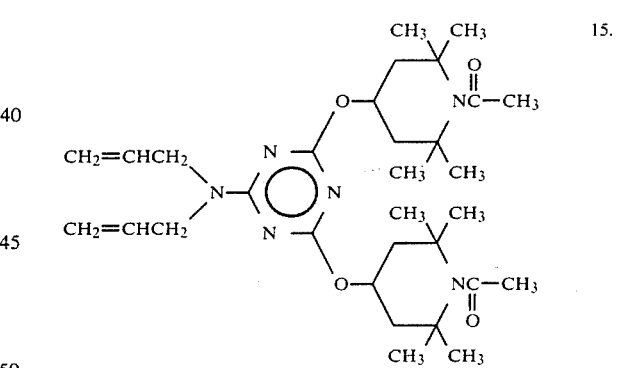
15.
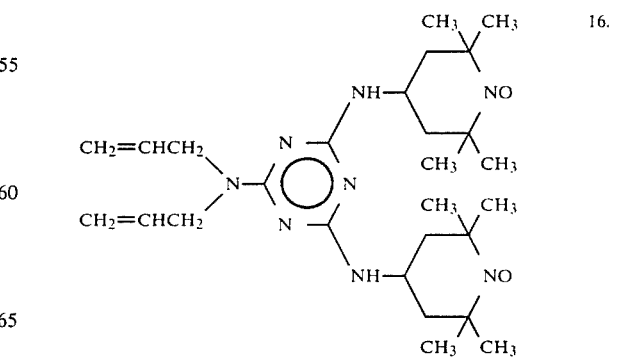
16.

-continued

17.

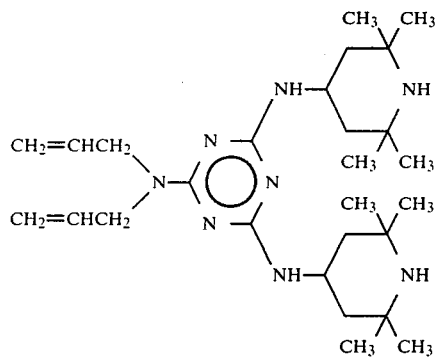

18.

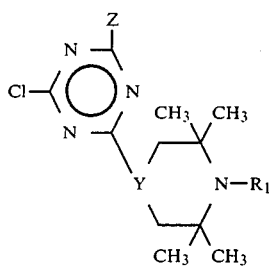

These compounds can be prepared by reaction of diallyl amine with monochlorotriazines of the formula

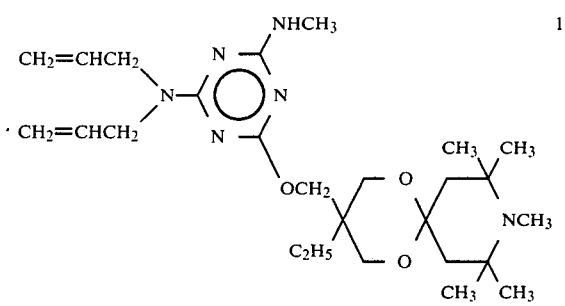

or reaction of diallylamino-dichlorotriazine with 2,2,6,6-tetramethylpiperidyl alcohol or amine (with H-Z).

The following Examples are illustrative:

EXAMPLE I

Preparation of (Polymer A)

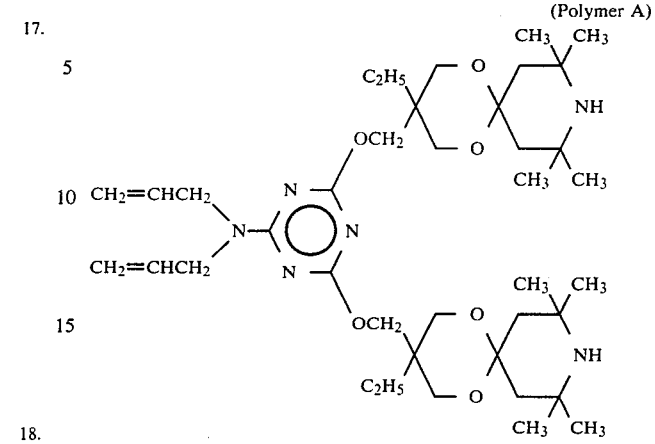

2-Diallylamino-4,6-dichloro-1,3,5-triazine 2.5 g, 9-aza-3-ethyl-3-hydroxymethyl-8,8,10,10-tetramethyl-1,5-dioxaspiro[5.5]undecane 6.2 g and toluene 30 ml were stirred and NaI 0.5 g and NaOH 1.2 g were added. The mixture was stirred for 24 hours while heating under reflux and then washed with water. The toluene was evaporated, and 8.0 g of product as a white powder of m.p. 76°–78° C. was obtained, IR; 920, 980, 1640 and 3090 cm$^{-1}$.

EXAMPLE II

Preparation of (Polymer B)

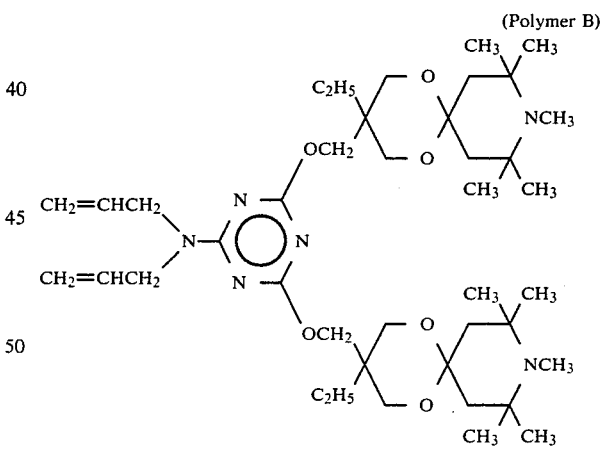

9-Aza-3-ethyl-3-hydroxymethyl-8,8,9,10,10-pentamethyl-1,5-dioxaspiro[5.5]undecane 6.2 g, 2-diallylamino-4,6-dichloro-1,3,5-triazine 2.5 g and toluene 30 ml were stirred and NaI 0.5 g and NaOH 1.2 g were added. The mixture was then heated and stirred for 24 hours under reflux. The whole was washed with water, and then toluene was distilled off. The product was obtained as a colorless liquid.

EXAMPLE III

Preparation of

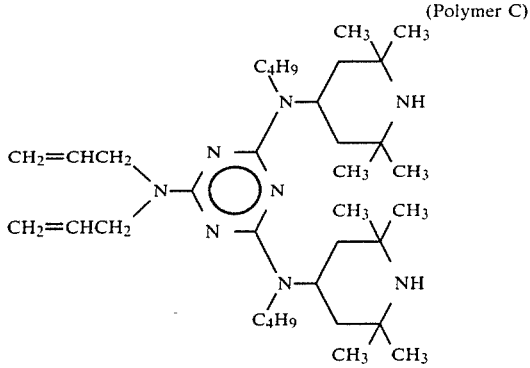
(Polymer C)

2-Diallylamino-4,6-dichloro-1,3,5-triazine 4.5 g, 2,2,6,6-tetramethyl-4-n-butylaminopiperidine 8.5 g and toluene 50 ml were stirred and NaOH 2.4 g was added. The mixture was then heated and stirred for 12 hours under reflux, and washed with water. Toluene was distilled off, and a white powder, m.p. 68°–70° C., was obtained.

The stabilizers of this invention are polymers of the monomeric diallylamines of Formula I. These polymers can easily be prepared by polymerization of the corresponding diallylamine in the presence of organic peroxide as an initiator.

The polymer has a molecular weight within the range from about 800 to about 20,000, preferably from about 1,000 to about 10,000.

Polymers of diallylamine compounds are known to have repeating units of

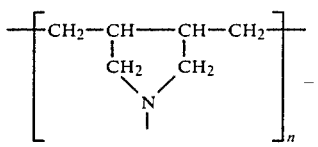

or

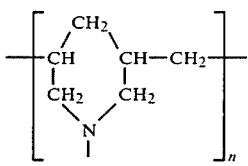

and the polymers of this invention also have such repeating units, with the free valence of the N attached to the 1,3,5-triazine-4-(2,2,6,6-tetramethyl piperidyl) group.

The polymers of this invention can be a homopolymer of the diallylamine of Formula I, or a copolymer of the diallylamine with another unsaturated monomer. Exemplary unsaturated monomers include, for example, ethylene, propylene, butene-1, isobutene, hexene, octene, decene, dodecene, tetradecene hexadecene, octadecene, eicosene, styrene, α-methylstyrene, cyclohexene, butadiene, vinyl chloride, acrylonitrile, methyl vinyl ketone, methyl vinyl ether, vinyl acetate, acrylic acid, methacrylic acid, maleic anhydride, methyl acrylate, butyl acrylate, methyl methacrylate, dimethyl maleate, diethyl maleate, dibutyl maleate, 2,2,6,6-tetramethyl-4-piperidiyl-vinyl ether, 1,2,2,6,6-pentamethyl-4-piperidyl-vinyl ether, 2,2,6,6-tetramethyl-4-piperidyl-allyl ether, 1,2,2,6,6-pentamethyl-4-piperidyl-allyl ether, 2,2,6,6-tetramethyl-4-piperidyl acrylate 1,2,2,6,6-pentamethyl-4-piperidyl acrylate, 8,8,10,10-tetramethyl-9-aza-3-ethyl-1,5-dioxaspiro[5.5]-3-undecylmethyl acrylate, 1,2,2,6,6-pentamethyl-4-piperidyl methacrylate, bis(1,2,2,6,6-pentamethyl-4-piperidyl)maleate, and bis(8,8,9,10,10-pentamethyl-9-aza-3-ethyl-1,5-dioxaspiro[5.5]-3-undecyl methyl)fumarate.

The molar ratio of the compound of Formula I to other unsaturated monomer is within the range from about 10:0 to 1:9.

Examples of the preparation of such polymers from the monomers of Formula I are shown below.

EXAMPLE A

Preparation of the polymer of

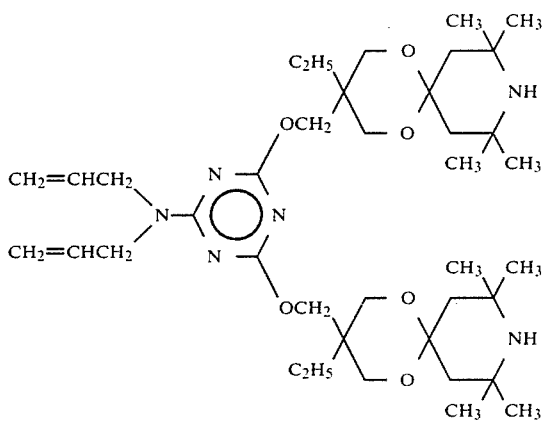

The above monomer 1.0 g, toluene 1 ml and dicumyl peroxide 50 mg were heated and stirred for 15 hours at 160°–180° C. Toluene 1 ml and dicumyl peroxide 20 mg were added twice at 5 hourly intervals.

Toluene 20 ml was added to the reaction mixture, which was then washed with water. Toluene was distilled off, and the polymer, a pale yellow powder having M.W. 7000–8000, was obtained.

EXAMPLE B

Preparation of the polymer of

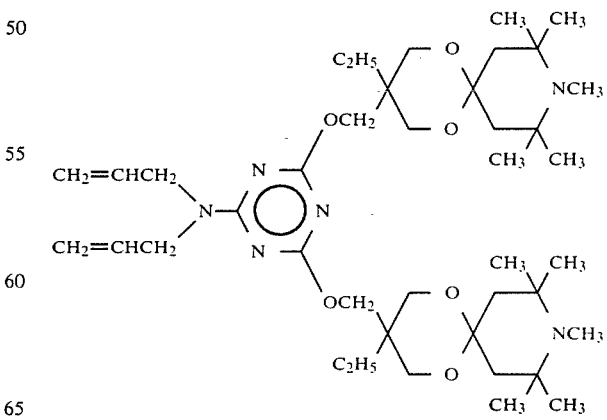

The monomer above, 1.0 g, PEGASOL 3040 5 ml and 2,5-dimethyl-2,5-di(t-butylperoxy)hexyne-3 40 ml were heated and stirred for 3 hours at 160°–180° C. and then toluene 20 ml was added. The reaction mixture was then washed with water. The solvent was distilled off, and the polymer, a white powder having M.W. 3000–4000, was obtained.

EXAMPLE C

Preparation of the polymer of

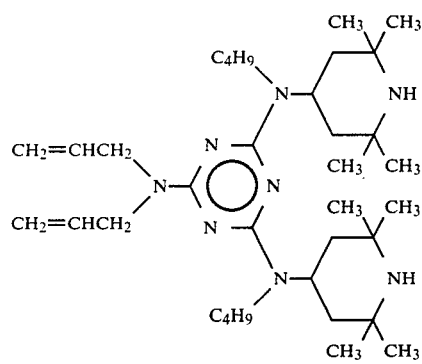

The above monomer, 1 g, toluene 1 ml and 2,5-dimethyl-2,5-di(t-butylperoxy)hexyne-3 50 mg were heated and stirred for 4 hours at 150°–160° C. Toluene 1 ml and 2,5-dimethyl-2,5-di(t-butylperoxy)hexyne-3 50 mg were added, and the mixture heated and stirred an additional 4 hours at 150°–160° C. Toluene 20 ml was added, and the mixture washed with water. Then, toluene was distilled off, and the polymer, a pale yellow powder having M.W. 7000–8000, was obtained.

The polymers shown below were prepared by the same procedure:

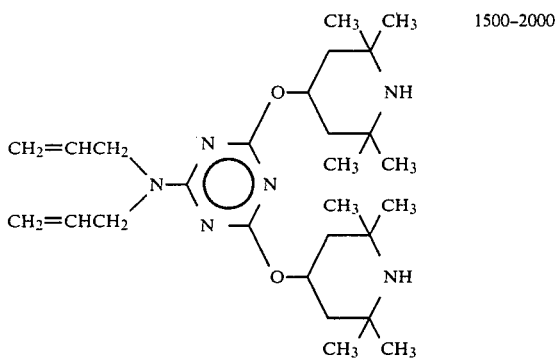

Small amounts of the polydiallyl-1,3,5-triazino-piperidyl amine of this invention when combined with synthetic resin improve the polydiallyl-1,3,5-triazinopiperidyl amine is generally within the range from about 0.001 to about 10 parts by weight, preferably from about 0.01 to about 3 parts by weight, per 100 parts by weight of resin.

Synthetic resins that can have their resistance to deterioration enhanced with polydiallyl-1,3,5-triazino-piperidyl amine according to this invention include α-olefin polymers such as polyethylene, polypropylene, polybutene, poly-3-methylbutene, or mixtures thereof and with copolymers other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The polydiallyl-1,3,5-triazino-piperidyl amines of the invention can be combined with conventional heat stabilizers such as phenolic antioxidants, polyvalent metal salts of organic acids, organic phosphites, thioethers, and other known heat stabilizers, thereby constituting light and heat stabilizers, compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclc phenols which can be employed have the structure:

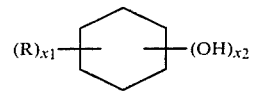

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

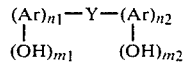

wherein Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

wherein R' is aryl, alkyl or cycloalkyl, or thiohydrocarbon groups having from one to about thirty carbon atoms, and carboxyl

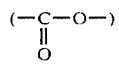

groups. Usually, however, each aromatic nucleus will not have more than about eighteencarbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

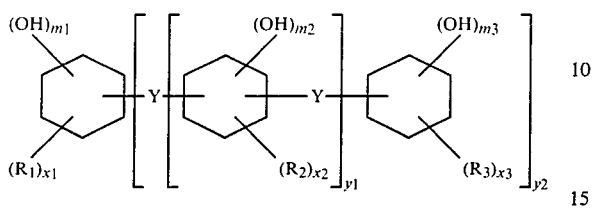

wherein $R_1$, $R_2$ and $R_3$ are inert substituent groups as described n the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

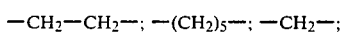

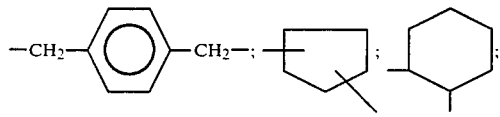

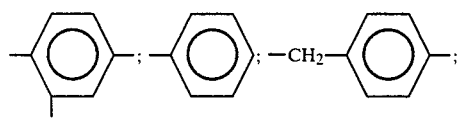

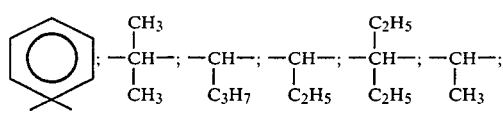

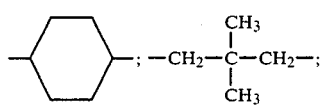

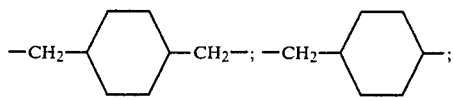

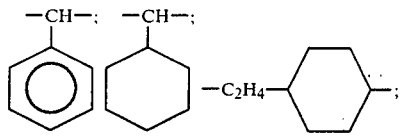

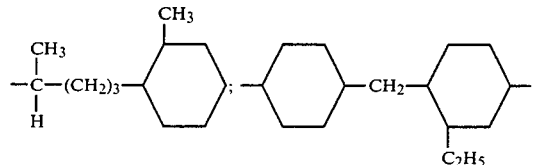

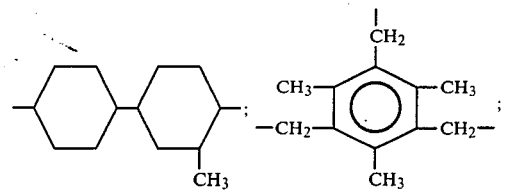

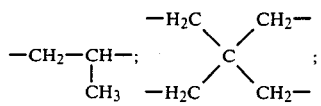

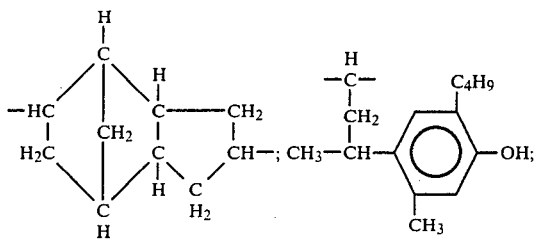

(2) Y groups where only atoms other than carbon link the aromatic rings, such as

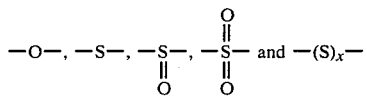

where x is a number from one to ten;

(3) Y groups made up of more than a single atom including both carbon and other atoms linking the aromatic nuclei, such as:

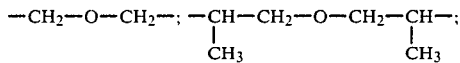

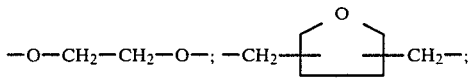

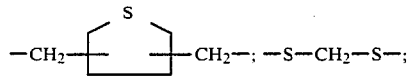

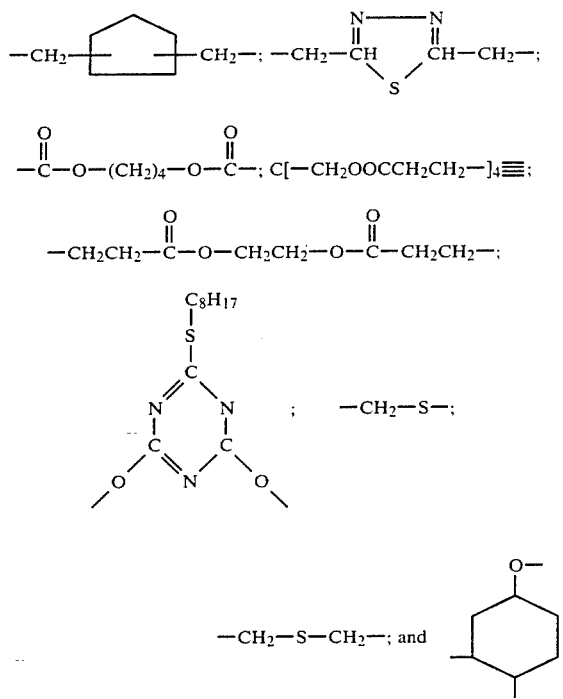

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl(4-hydroxy-3-methyl-5-t-butyl)benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis(2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-b 4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis(naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)-(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazole-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butane-dio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methylbenzene-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butyl-phenyl)butyric acid]glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3(3,5-di-t-butyl-4-hydroxyphenyl)propionate]methane, 1,3,5-tris-(3,5-di-t-butyl-4-hydroxybenzyl)isocyanurate, 1,3,5-tris-(3,5-di-t-butyl-4-hydroxyphenyl)propionyloxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

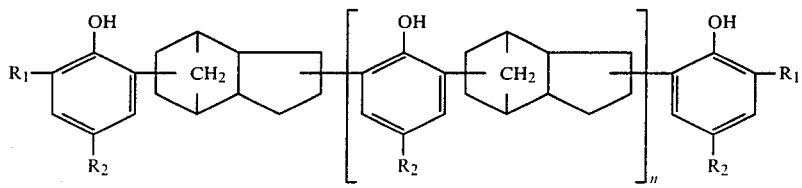

in which
R₁ and R₂ are lower alkyl, and can be the same or different, and
n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

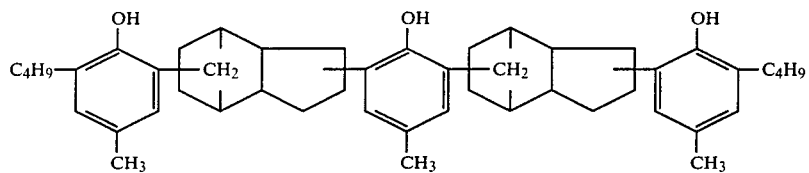

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogens, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

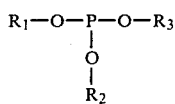

in which R₁, R₂ and R₃ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

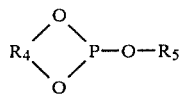

in which
R$_4$ is a bivalent organic radical selected from the group consisting of alkylene, arylene, aralkylene, alkarylene and cycloalkylene radicals having from two to about thirty carbon atoms, and R$_5$ is a monovalent organic radical as defined above in the case of R$_1$, R$_2$ and R$_3$;
R$_5$ is hydrogen or a cation, in the case of the acid phosphites.

Also useful organic triphosphites are mixed heterocyclic-open chain phosphites of the type:

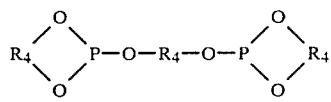

More complex triphosphites are formed from trivalent organic radicals, of the type:

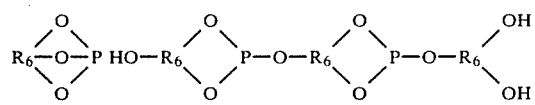

in which R$_6$ is a trivalent organic radical of any of the types of R$_1$ to R$_5$, inclusive, as defined above.

A particularly useful class of complex triphosphites are the tetraoxadiphosphaspiro undecanes of the formula:

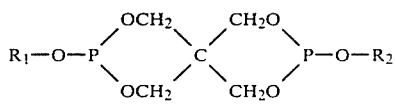

wherein R$_1$ and R$_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of R$_1$ and R$_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula;

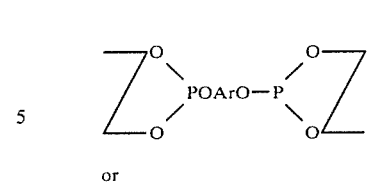

or

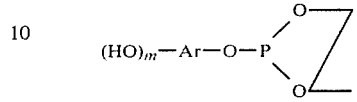

in which Ar is a mono or bicyclic aromatic nucleus and m is an integer of from 0 to about 5. Z is one or a plurality of organic radicals as defined above for R$_1$ to R$_6$, taken singly or together in sufficient number to satisfy the valences of the two phosphite oxygen atoms.

One or both Z radicals is also hydrogen, in the case of the acid phosphites, and can include additional bicyclic aromatic groups of the type (HO)$_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phoshite, tri(phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane(diphenyl-pentaerythritol diphosphite), 3,9-di(decyloxy)-2,4,8,10-tetroxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9- butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy)ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-thio-bis(2-tertiary-butyl-5-methyl-phenol))di-phenyl phosphite, tri-(4,4'-n-butylidene-bis-(2-tertiary-butyl-5-methyl-phenol))phosphite, (4,4'-benzylidene-bis(2-tertiary-butyl-5-methyl-phenol))diphenyl phosphite, isooctyl 2,2'-bis(-para-hydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)-phenol phosphite, tri(2,2'-bis-(para-hydroxyphenyl)-propane)phosphite, tri(4,4'-thio-bis(2-tertiary-butyl-5-methyl-phenol)phosphite, isooctyl-(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bis-phenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, decresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))-phosphite, (4,4'-thio-bis(2-tertiary-butyl-5-methyl-phenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenol))phosphite, mono-2-ethyl-hexyl-mono-2,2'-methylene-bis(4-methyl-6,1'-methylcyclohexyl)phenol phosphite, bis(2,2'-bis(para-hydroxyphenyl)propane)phosphite, monoisooctylmono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, trii-sooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

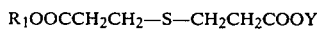

$R_1OOCCH_2CH_2{-}S{-}CH_2CH_2COOY$ in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same or different from the $R_1$ radical, (c) a polymeric chain of n thiodipropionic acid ester units:

$-XO[OCCH_2CH_2SCH_2CH_2COOXO]_nOCCH_2CH_2{-}S{-}CH_2CH_2COOZ$ where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylene-cycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
 (a) $R_1OOCCH_2CH_2SCH_2CH_2COOH$
 (b) $R_1OOCCH_2CH_2SCH_2CH_2COOR_2$
 (c) $R_1O[OCCH_2CH_2SCH_2CH_2COOX{-}O]_nOCCH_2CH_2SCH_2CH_2COOZ$
 (d) $R_1OOCCH_2CH_2SCH_2CH_2COOM$ In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, R₂ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethylhexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

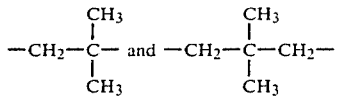

arylene radicals such as phenylene methylenephenylene —CH₂— dimethylene phenylene —CH₂— —CH₂— and alicyclylene such as cyclohexylene and cyclopentylene 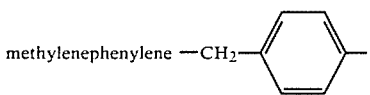

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionte, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most known compounds, but where they are not available, they are readily prepared by esterification of thiodipropionic acid and the corresponding alcohol.

Also useful are:

(1) Thiolkanoic acid amides of Tokuno et al Japanese Pat. No. 16,286/68 having the formula:

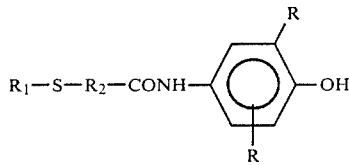

R is alkyl of one to eight carbon atoms, R₁ is alkyl of six to twenty-four carbon atoms, and R₂ is alkylene of one to six carbon atoms.

(2) Thioalkanoic acid amides of 1,3,5-triazines of Ozeki et al Japanese Pat. No. 20,366/68 having the formula:

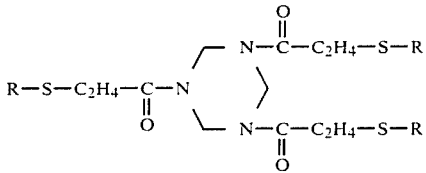

R is alkyl of eight to eighteen carbon atoms.

(3) Bis-thioalkanoic acid amides of Yamamoto et al Japanese Pat. No. 23,765/68 having the formula:

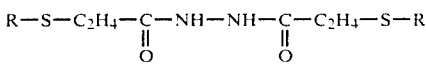

R is alkyl of more than six carbon atoms, aryl or aralkyl.

(4) Bis-thioalkylanoic acid amides of Ozeki et al Japanese Pat. No. 26,184/69 having the formula:

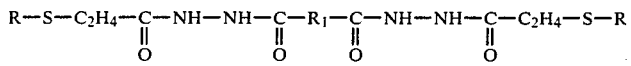

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

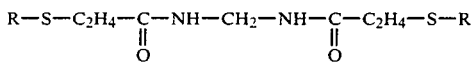

R is alkyl of more than six carbon atoms, aryl, or aralkyl.

(6) Thioalkanoic acid amide derivatives of Minagawa et al, published Japanese application No. 106,484/74 having the formula:

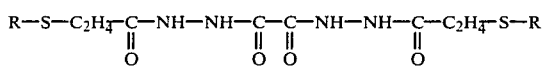

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

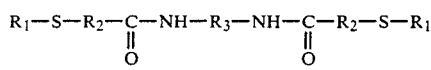

wherein:
$R_1$ is alkyl having from one to about fifty carbon atoms;
$R_2$ is alkylene having from one to about three carbon atoms; and
$R_3$ is alkylene having from about two to about twelve carbon atoms.

β-Alkylthiopropionic acid esters having the general formula:

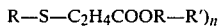

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxybenzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl)5-chlorobenzotriazole, 2(2-hydroxy-3,5-di-t-amylphenyl)benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octyl-phenolate), nickel-monoethyl(3,5-di-t-butyl-4-hydroxybenzyl)phosphonate, substituted acrylonitriles such as methyl-α-cyano-β-methyl-β-(p-methoxy phenyl)acrylate and oxalic anilides such as N-2-ethylphenyl-N'-2-ethoxy-5-t-butylphenyl oxalic diamide, N-2-ethylphenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 5% total stabilizers including the polydiallyl-1,3,5-triazino-piperidyl amine of the invention by weight of the polymer are satisfactory. Preferably, from 0.01 to 3% is employed for optimum stabilization.

The stabilizer systems of the invention are readily rendered in solid particulate form, comprising a blend of:

(a) polydiallyl-1,3,5-triazino-piperidyl amine light stabilizer in an amount of from about 10 to about 35 parts by weight; and optionally:

(b) a phenolic antioxidant in an amount from about 10 to about 35 parts by weight; and/or (c) other heat or light stabilizers in an amount of from about 10 to about 35 parts by weight.

The polydiallyl-1,3,5-triazino-piperidyl amine light stabilizer of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples in the opinion of the inventors represent preferred embodiments of synthetic resin compositions containing the polydiallyl-1,3,5-triazino-piperidyl amine light stabilizers of the invention.

EXAMPLES 1 TO 5

Polypropylene compositions were prepared using a stabilizer of the invention and two of the prior art, and having the following formulation:

| Ingredient | Parts by Weight |
|---|---|
| Polypropylene | 100 |
| Stearyl β-3,5-di-t-butyl-4-hydroxyphenyl propionate | 0.2 |
| Stabilizer as shown in Table I | 0.3 |

The compositions were thoroughly blended in a Brabender Plastograph, and then compression-molded to form sheets 0.3 mm thick. Pieces 2.5 cm² were cut off from the sheets and exposed to a high voltage mercury lamp and with and without immersion in hot water at 80° C. for fifteen hours. The hours to failure were noted and the results are shown in Table I.

TABLE I

| | Stabilizer | Hours to Failure | |
|---|---|---|---|
| | | Without Immersion | After Immersion for 15 hours |
| Control 1 | N,N',N'',N'''—Tetrakis[2,4-bis[N—(2,2,6,6-tetramethyl-4-piperidyl)butylamino]-1,3,5-triazine-6-yl]triethylenetetramine | 560 | 460 |
| Control 2 | N,N'—Bis(2,2,6,6-tetramethyl-4-piperidyl)hexamethylene-diamine/1,2-dibromethane condensate (M.W. 3000–4000) | 510 | 430 |
| Example 1 | Polymer of | 830 | 770 |

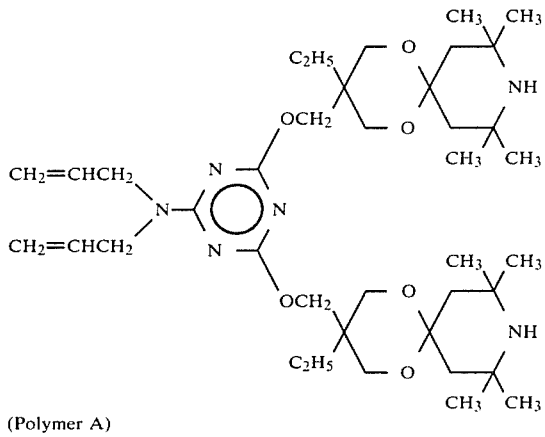

(Polymer A)

| Example 2 | Polymer of | 820 | 760 |

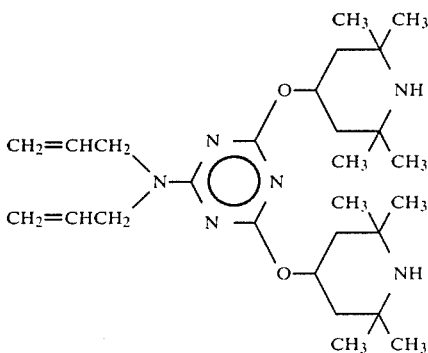

(Polymer D, M.W. 1500–2000)

| Example 3 | Polymer of | 800 | 730 |

TABLE I-continued

| | | Hours to Failure | |
|---|---|---|---|
| Stabilizer | | Without Immersion | After Immersion for 15 hours |
| (Polymer C) | | | |
| Example 4 Polymer of (Polymer G, M.W. 7000-8000) | | 820 | 750 |
| Example 5 Polymer of (Polymer H) | | 770 | 690 |

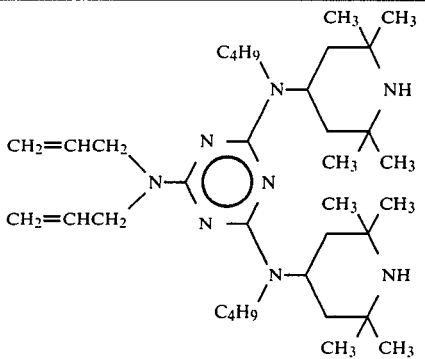
(Polymer C)

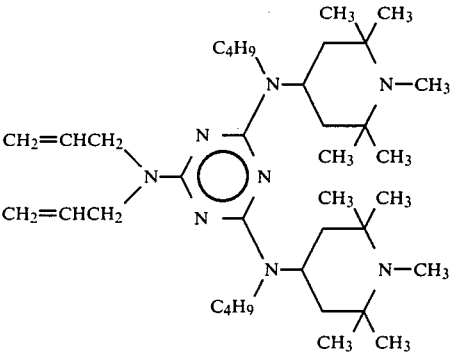
(Polymer G, M.W. 7000-8000)

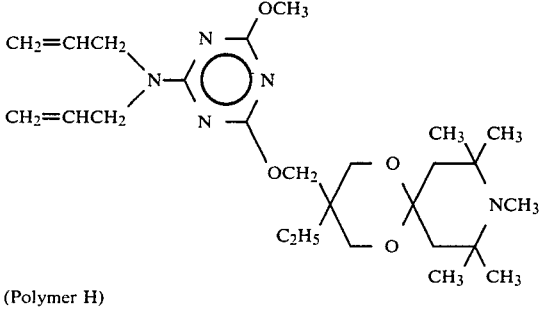
(Polymer H)

The superiority of the stabilizer of the invention is apparent from the above data.

EXAMPLES 6 TO 8

Conventional stabilizers for polymeric materials may lose their effectiveness because of volatilization or decomposition at high polymer processing temperatures. This is not true of the stabilizers of the invention, as shown by observing the effect of heat in repeated extrusions of ethylenepropylene copolymer compositions. These compositions were prepared using a stabilizer of the invention and of the prior art, and having the following formulation:

| Ingredient | Parts by Weight |
|---|---|
| Ethylene-propylene copolymer | 100 |
| Ca stearate | 0.2 |
| Stearyl-(3,5-di-t-butyl-4-hydroxyphenyl)propionate | 0.1 |
| Dilauryl thiodipropionate | 0.2 |
| Stabilizer as shown in Table II | 0.2 |

The ingredients were mixed and the compositions then extruded (cylinder temperature 230° C. and 240° C., head die temperature 250° C., velocity 20 rpm) five times. Test pieces were then molded by injection molding at 250° C. The test pieces were exposed to a high voltage mercury lamp, and the hours to failure noted as shown in Table II.

TABLE II

| | Stabilizer | Hours to Failure | |
|---|---|---|---|
| | | Extruded 1 time | Extruded 5 times |
| Control 1 | N,N′,N″,N‴—Tetrakis[2,4-bis[N—(2,2,6,6-tetramethyl-4-piperidyl)butylamino]-1,3,5-triazine-6-yl]triethylenetetramine | 490 | 430 |
| Control 2 | N,N′—Bis(2,2,6,6-tetramethyl-4-piperidyl)hexamethylene-diamine/1,2-dibromethane condensate (M.W. 3000-4000) | 460 | 340 |
| Example 6 | Polymer of 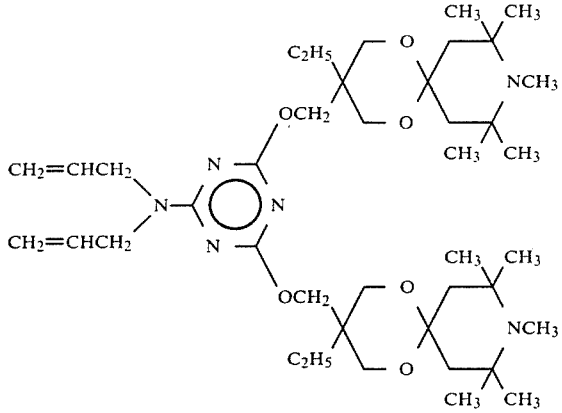 (Polymer B) | 660 | 600 |
| Example 7 | Polymer of 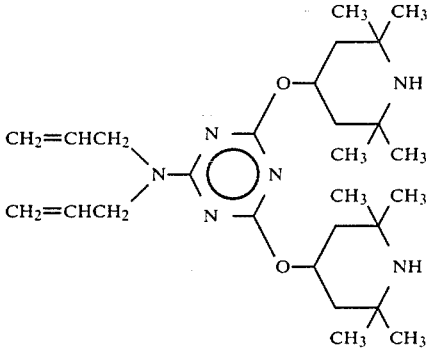 (Polymer E, M.W. 3000-4000) | 630 | 560 |
| Example 8 | Polymer of 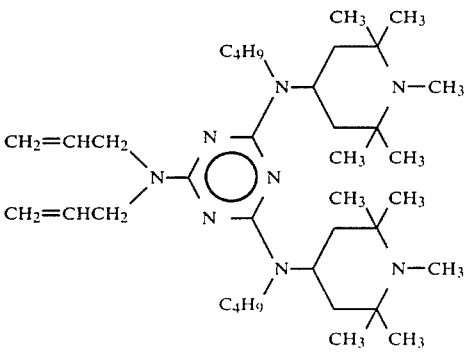 (Polymer F, M.W. 4000-5000) | 630 | 570 |

The superiority of the stabilizer of the invention is apparent from the above data.

High density polyethylene compositions were prepared using a stabilizer of the invention and two of the prior art, and having the following formulation:

| Ingredient | Parts by Weight |
| --- | --- |
| High-density polyethylene | 100 |
| Ca stearate | 1 |
| Tetrakis-(methylene-3-(3,5-di-t-butyl-4-hydroxyphenyl) propionate) methane | 0.1 |
| Distearylthiodipropionate | 0.3 |

| Ingredient | Parts by Weight |
| --- | --- |
| Stabilizer as shown in Table III | 0.2 |

The stabilizer was blended with the polymer on a two-roll mill and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table III:

TABLE III

| | Stabilizer | Hours to Failure |
| --- | --- | --- |
| Control 1 | N,N',N'',N'''—Tetrakis [2,4-bis[N—(2,2,6,6-tetramethyl-4-piperidyl) butylamino]-1,3,5-triazine-6-yl] triethylenetetramine | 780 |
| Control 2 | N,N'—Bis(2,2,6,6-tetramethyl-4-piperidyl) hexamethylenediamine/1,2-dibromethane condensate (M.W. 3000–4000) | 710 |
| Example 9 | Polymer of 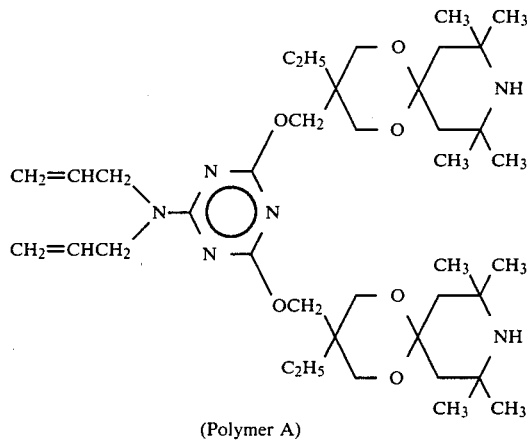 (Polymer A) | 1220 |
| Example 10 | Polymer of 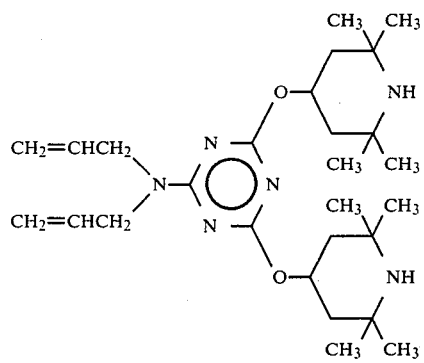 (Polymer D, M.W. 1500–2000) | 1180 |
| Example 11 | Polymer of | 1160 |

TABLE III-continued

| Stabilizer | Hours to Failure |
|---|---|

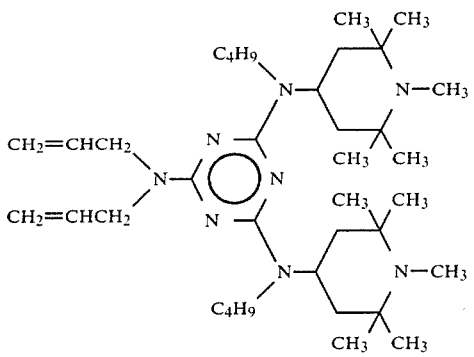

(Polymer G. M.W. 7000-8000)

The superiority of the stabilizer of the invention is apparent from the above data.

EXAMPLES 12 TO 14

Ethylene-vinyl acetate copolymer compositions were prepared using a stabilizer of the invention and two of the prior are, and having the following formulation:

| Ingredient | Parts by Weight |
|---|---|
| Ethylene vinyl acetate copolymer | 100 |
| 2,6-di-t-butyl-p-cresol | 0.1 |
| Ca stearate | 0.1 |
| Zn stearate | 0.1 |
| Diisodecylphenyl phosphite | 0.2 |
| Stabilizer as shown in Table IV | 0.2 |

The stabilizer was blended with the polymer on a two-roll mill at 130° C. and sheets 0.4 mm thick were then compression-molded at 140° C. from the resulting blend. Pieces 2.5 cm square were cut off from the sheets and exposed to ultraviolet light in a Weather-O-Meter for 500 hours. At the start and at the conclusion of the test, tensile strength of the sheet samples was determined. The results are shown in Table IV as percent retention of the initially determined tensile strength:

TABLE IV

| | Stabilizer | % Retention of Tensile Strength After 500 Hours |
|---|---|---|
| Control 1 | N,N',N'',N'''—Tetrakis[2,4-bis[N—(2,2,6,6-tetramethyl-4-piperidyl) butylamino]-1,3,5-triazine-6-yl] triethylenetetramine | 73 |
| Control 2 | N,N'—Bis(2,2,6,6-tetramethyl-4-piperidyl) hexamethylenediamine/1,2-dibromethane condensate (M.W. 3000-4000) | 69 |
| Example 12 | Polymer of | 83 |

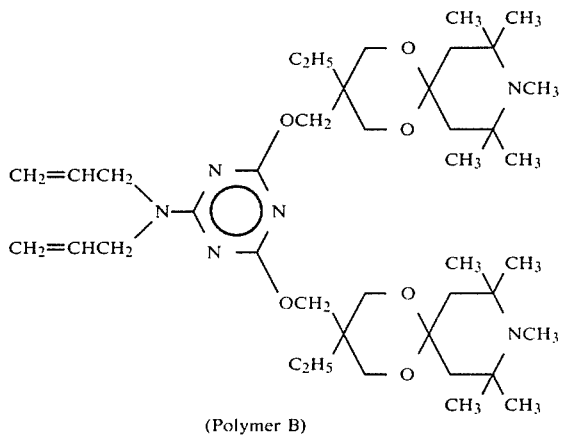

(Polymer B)

| Example 13 | Polymer of | 82 |

TABLE IV-continued

| Stabilizer | % Retention of Tensile Strength After 500 Hours |
|---|---|
| 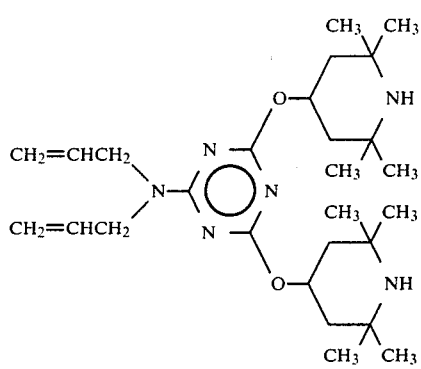 (Polymer E. M.W. 3000-4000) | |
| Example 14 Polymer of 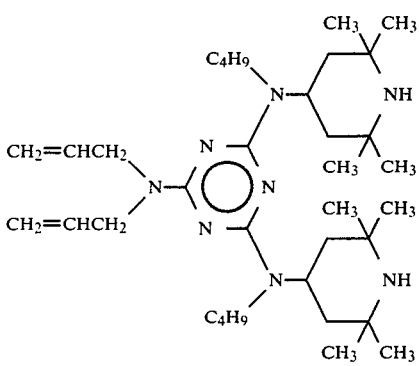 (Polymer C) | 80 |

The superiority of the stabilizer of the invention is apparent from the above data.

EXAMPLES 15 TO 16

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2 |
| Tris(nonyl phenyl) phosphite | 0.2 |
| Ca stearate | 1.0 |
| Zn stearate | 0.1 |
| Stabilizer as shown in Table V | 0.3 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

The following results were obtained:

TABLE V

| | Stabilizer | Hours to Failure |
|---|---|---|
| Control 1 | None | 180 |
| Control 2 | N,N',N'',N'''—Tetrakis[2,4-bis[N—(2,2,6,6-tetramethyl-4-piperidyl)butylamino]-1,3,5-triazine-6-yl]triethylenetetramine | 550 |
| Control 3 | N,N'—Bis(2,2,6,6-tetramethyl-4-piperidyl)hexamethylenediamine/1,2-dibromethane condensate (M.W. 3000-4000) | 520 |
| Example 15 | Polymer of | 830 |

TABLE V-continued

| Stabilizer | Hours to Failure |
|---|---|

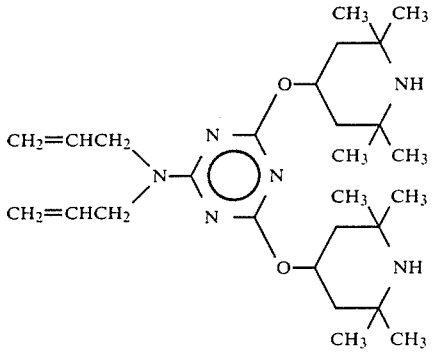

(Polymer D, M.W. 1500-2000)

Example 16  Polymer of    820

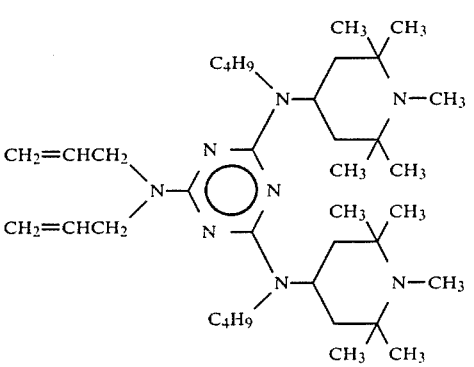

(Polymer F, M.W. 4000-5000)

The superiority of the stabilizer of the invention is apparent from the above data.

EXAMPLES 17 TO 19

Acrylonitrile-butadiene-styrene terpolymer resin compositions were prepared using a stabilizer of the invention and two of the prior art, and having the following formulations:

| Ingredient | Parts by Weight |
|---|---|
| Acrylonitrile-butadiene-styrene terpolymer | 100 |
| 4,4'-Butylidene-bis(2-t-butyl-m-cresol) | 0.1 |

-continued

| Ingredient | Parts by Weight |
|---|---|
| Stabilizer as shown in Table VI | 0.3 |

The stabilizer was blended with the resin on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the text exposure was determined, and the results reported as the percent of tensile strength retained, at the end of this time, in Table VI.

TABLE VI

| | Stabilizer | % Tensile Strength Retained |
|---|---|---|
| Control 1 | N,N',N'',N'''—Tetrakis[2,4-bis[N—(2,2,6,6-tetramethyl-4-piperidyl)butylamino]-1,3,5-triazine-6-yl]triethylenetetramine | 66 |
| Control 2 | N,N'—bis(2,2,6,6-tetramethyl-4-piperidyl)hexamethylenediamine/1,2-dibromethane condensate (M.W. 3000-4000) | 61 |
| Example 17 | Polymer of | 85 |

TABLE VI-continued

| Stabilizer | % Tensile Strength Retained |
|---|---|
| 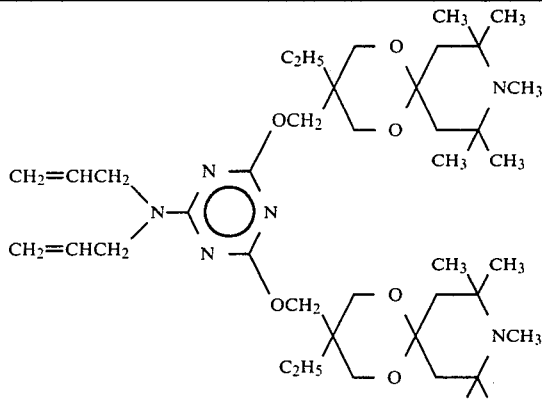<br>(Polymer B)<br>Example 18 Polymer of | 84 |
| 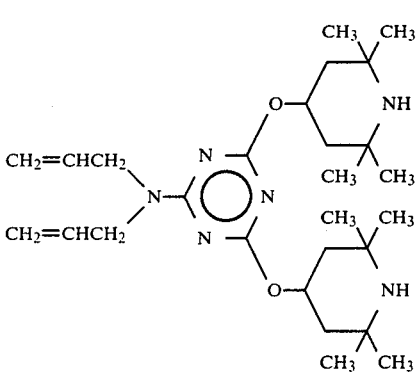<br>(Polymer E, M.W. 3000-4000)<br>Example 19 Polymer of | 85 |
| 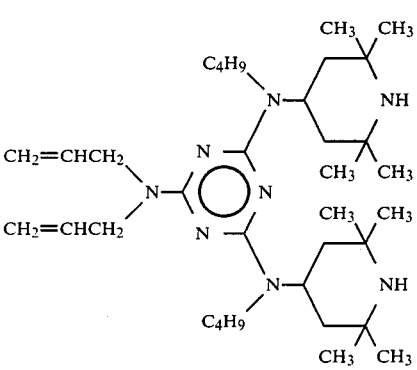<br>(Polymer C) | |

The superiority of the stabilizer of the invention is apparent from the above data.

EXAMPLES 20 TO 22

Polyurethane resin compositions were prepared using a stabilizer of the invention and having the following formulation:

| Ingredient | Parts by Weight |
|---|---|
| Polyurethane resin (Asahi Denka U-100)[1] | 100 |
| Ca stearate | 0.7 |
| Zn stearate | 0.3 |
| 2,6-di-t-butyl-p-cresol | 0.1 |
| Stabilizer as shown in Table VII | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm square were cut out from the sheets, and exposed to ultraviolet light in a Weather-O-Meter for thirty hours. Elongation before and after exposure was determined, and the percent elongation retained after the exposure is given in Table VII.

quer, and a unpigmented finishing lacquer, was determined.

(a) Metallic effect priming lacquer

Methyl methacylate 100 g, n-butylacrylate 66 g, 2-hydroxyethyl methacrylate 30 g, methacrylic acid 4 g, xylene 80 g and n-butanol 20 g were heated and stirred at 110° C., and a solution of azo-bis(isobutyronitrile) 2 g, dodecylmercaptan 0.5 g, xylene 80 g and n-butanol 20 g was added dropwise over 3 hours.

The solution was stirred an additional 2 hours at 110° C. The resulting acylic resin solution, 12 parts, butoxylated methylolmelamine (Mitsui-Toatsu Co., Yuban 20SE60; solids content 60%) 2.5 parts; cellulose acetobutyrate (20% butylacetate solution) 50 parts; aluminium pigment (Toyo Alminium Co., Alpaste 1123N) 5.5

TABLE VII

| | Stabilizer | % Elongation Retained |
|---|---|---|
| Control 1 | N,N',N'',N'''—Tetrakis[2,4-bis[N—(2,2,6,6-tetramethyl-4-piperidyl)butylamino]-1,3,5-triazine-6-yl]triethylenetetramine | 60 |
| Control 2 | N,N'—Bis(2,2,6,6-tetramethyl-4-piperidyl)hexamethylenediamine/1,2-dibromethane condensate (M.W. 3000–4000) | 58 |
| Example 20 | Polymer of (structure shown) (Polymer D. M.W. 1500–2000) | 76 |
| Example 21 | Polymer of (structure shown) (Polymer C) | 78 |
| Example 22 | Polymer of (structure shown) (Polymer H) | 74 |

The superiority of the stabilizer of the invention is apparent from the above data.

EXAMPLES 23 TO 24

The stabilizers of this invention are effective as light stabilizer for coatings.

The effect of the stabilizer in a two-coat metallic effect finish, comprising a metallic effect priming lacparts, butylacetate 20 parts; and copper phthalocyanine blue 0.2 parts were blended.

(b) Unpigmented finishing lacquer

The above acrylic resin solution 48 parts; butoxylated-methylolmelamine 10 parts; xylene 10 parts; butoxyethylacetate 4 parts; and stabilizer as shown in Table VIII 0.15 part; were blended.

Pieces of steel sheeting which were coated with a primer, were first coated with the priming lacquer, and subsequently coated with the finishing lacquer. The priming lacquer was sprayed on to a thickness of about $20\mu$, and aired for 10 minutes. Then the clear lacquer was sprayed on, to a thickness of about $30\mu$. After being aired 15 minutes, the samples were heated in an oven for 30 minutes at 140° C.

The coated sheets were exposed to ultraviolet light in a Weather-O-Meter. The time in hours when degradation set in, as determined by cracking on the surface of sheet, was noted as hours to failure, and the results are shown in Table VIII.

Having regard to the foregoing disclosure, the following is claimed as the inventive and patentable embodiments thereof:

1. Diallyl-1,3,5-triazino-4-(2,2,6,6-tetramethyl piperidyl)amines having the formula:

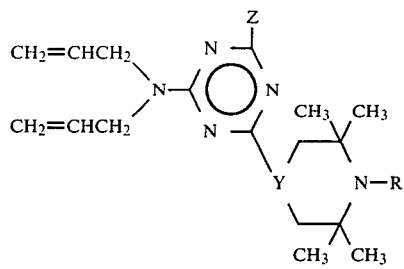

wherein:

R is selected from the group consisting of hydrogen; oxyl; alkyl and hydroxyalkyl having from one to about eighteen carbon atoms; alkylaryl having

TABLE VIII

| | Stabilizer | Hours to Failure |
|---|---|---|
| Control 1 | None | 1600 |
| Control 2 | N,N',N'',N'''—Tetrakis[2,4-bis[N—(2,2,6,6-tetramethyl-4-piperidyl)butylamino]-1,3,5-triazine-6-yl]triethylenetetramine | 2800 |
| Control 3 | N,N'—Bis(2,2,6,6-tetramethyl-4-piperidyl)hexamethylenediamine/1,2-dibromethane condensate (M.W. 3000–4000) | 2400 |
| Example 23 | Polymer of (Polymer A) | 4300 |
| Example 24 | Polymer of (Polymer G, M.W. 7000–8000) | 4500 |

The superiority of the stabilizer of the invention is apparent from the above data.

from seven to about eighteen carbon atoms; epoxy alkyl having from three to about eighteen carbon atoms; and acyl having from two to about eighteen carbon atoms;

Y is

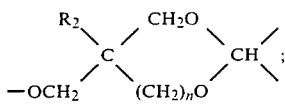

where $R_2$ and $R_3$ are hydrogen or alkyl having from one to about eight carbon atoms and n is 0 or 1;

Z is selected from the group consisting of

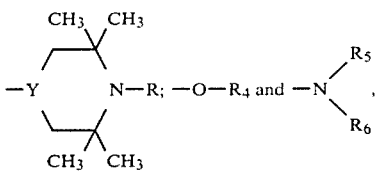

in which $R_4$, $R_5$ and $R_6$ are selected from the group consisting of hydrogen; alkyl having from one to about eighteen carbon atoms; cycloalkyl having from three to about twelve carbon atoms; and aryl having from six to about thirty carbon atoms.

2. Diallyl-1,3,5-triazino-4-(2,2,6,6-tetramethyl piperidyl)amines according to claim 1 in which R is hydrogen.

3. Diallyl-1,3,5-triazino-4-(2,2,6,6-tetramethyl piperidyl)amines according to claim 1 in which R is alkyl.

4. Diallyl-1,3,5-triazino-4-(2,2,6,6-tetramethyl piperidyl)amines according to claim 1 in which R is acyl.

5. Diallyl-1,3,5-triazino-4-(2,2,6,6-tetramethyl piperidyl)amines according to claim 1 in which R is epoxyalkyl.

6. Diallyl-1,3,5-triazino-4-(2,2,6,6-tetramethyl piperidyl)amines according to claim 1 in which R is alkylaryl.

7. Diallyl-1,3,5-triazino-4-(2,2,6,6-tetramethyl piperidyl)amines according to claim 1 in which Y is OCH<.

8. Diallyl-1,3,5-triazino-4-(2,2,6,6-tetramethyl piperidyl)amines according to claim 1 in which Y is

9. Diallyl-1,3,5-triazino-4-(2,2,6,6-tetramethyl piperidyl)amines according to claim 1 in which Y is

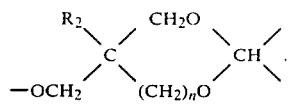

10. Diallyl-1,3,5-triazino-4-(2,2,6,6-tetramethyl piperidyl)amines according to claim 1 in which Z is

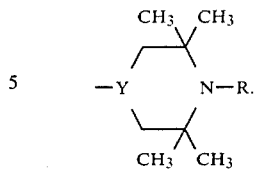

11. Diallyl-1,3,5-triazino-4-(2,2,6,6-tetramethyl piperidyl)amines according to claim 1 in which Z is $-OR_4$.

12. Diallyl-1,3,5-triazino-4-(2,2,6,6-tetramethyl piperidyl)amines according to claim 1 in which Z is

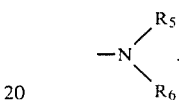

13. Polymers of diallyl-1,3,5-triazino-4-(2,2,6,6-tetramethyl piperidyl)amines according to claim 1, having a molecular weight within the range from about 800 to about 20,000.

14. Polymers of diallyl-1,3,5-triazino-4-(2,2,6,6-tetramethyl piperidyl)amines according to claim 13 in which R is hydrogen.

15. Polymers of diallyl-1,3,5-triazino-4-(2,2,6,6-tetramethyl piperidyl)amines according to claim 13 in which R is alkyl.

16. Polymers of diallyl-1,3,5-triazino-4-(2,2,6,6-tetramethyl piperidyl)amines according to claim 13 in which R is acyl.

17. Polymers of diallyl-1,3,5-triazino-4-(2,2,6,6-tetramethyl piperidyl)amines according to claim 13 in which R is epoxyalkyl.

18. Polymers of diallyl-1,3,5-triazino-4-(2,2,6,6-tetramethyl piperadyl)amines according to claim 13 in which R is alkylaryl.

19. Polymers of diallyl-1,3,5-triazino-4-(2,2,6,6-tetramethyl piperidyl)amines according to claim 13 in which Y is —OCH<.

20. Polymers of diallyl-1,3,5-triazino-4-(2,2,6,6-tetramethyl piperidyl)amines according to claim 13 in which Y is

21. Polymers of diallyl-1,3,5-triazino-4-(2,2,6,6-tetramethyl piperidyl)amines according to claim 13 in which Y is

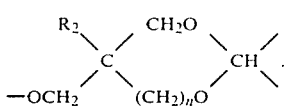

22. Polymers of diallyl-1,3,5-triazino-4-(2,2,6,6-tetramethyl piperidyl)amines according to claim 13 in which Z is

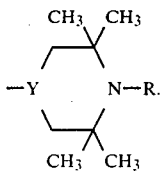

23. Polymers of diallyl-1,3,5-triazino-4-(2,2,6,6-tetramethyl piperidyl)amines according to claim 13 in which Z is OR$_4$.

24. Polymers of diallyl-1,3,5-triazino-4-(2,2,6,6-tetramethyl piperidyl)amines according to claim 13 in which Z is

25. A polyvinyl chloride resin composition having improved resistance to deterioration when exposed to light, comprising a polyvinyl chloride resin formed at least in part of the recurring group:

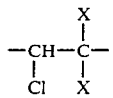

and having a chlorine content in excess of 49%, where X is either hydrogen or chlorine, and an amount sufficient to improve resistance to deterioration of the resin of a compound in accordance with claim 13.

26. A polyvinyl chloride resin composition in accordance with claim 25 in which the polyvinyl chloride resin is polyvinyl chloride homopolymer.

27. A polyvinyl chloride resin composition in accordance with claim 25 in which the polyvinyl chloride resin is a copolymer of vinyl chloride and vinyl acetate.

28. An olefin polymer composition having improved resistance to deterioration comprising an olefin polymer selected from the group consisting of polymers of alphaolefins having from two to six carbon atoms and polystyrene, and an amount sufficient to improve resistance to deterioration of the resin of a compound in accordance with claim 13.

29. An olefin polymer composition in accordance with claim 28 wherein the polyolefin is polypropylene.

30. An olefin polymer composition in accordance with claim 28 wherein the polyolefin is polyethylene.

31. An olefin polymer composition in accordance with claim 28 wherein the polyolefin is ethylene-propylene copolymer.

32. An acrylonitrile-butadiene-styrene polymer having improved resistance to deterioration when exposed to light comprising an acrylonitrile-butadiene-styrene polymer and an amount sufficient to improve resistance to deterioration of the resin of a compound in accordance with claim 13.

33. A polyurethane resin composition having improved resistance to deterioration comprising a polyurethane resin and an amount sufficient to improve resistance to deterioration of the resin of a compound in accordance with claim 13.

* * * * *